United States Patent
Syfonios et al.

(10) Patent No.: US 10,729,837 B2
(45) Date of Patent: Aug. 4, 2020

(54) DIALYSIS MACHINE

(71) Applicant: FRESENIUS MEDICAL CARE DEUTSCHLAND GMBH, Bad Homburg (DE)

(72) Inventors: Andreas Syfonios, Bergrheinfeld (DE); Tilman Staeblein, Wuerzburg (DE); Dirk Huemmer, Hirschfeld (DE); Peter Kloeffel, Nuedlingen (DE)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 0 days.

(21) Appl. No.: 15/763,260

(22) PCT Filed: Sep. 28, 2016

(86) PCT No.: PCT/EP2016/001613
§ 371 (c)(1),
(2) Date: Mar. 26, 2018

(87) PCT Pub. No.: WO2017/054923
PCT Pub. Date: Apr. 6, 2017

(65) Prior Publication Data
US 2018/0272054 A1 Sep. 27, 2018

(30) Foreign Application Priority Data
Sep. 28, 2015 (DE) .................. 10 2015 012 604

(51) Int. Cl.
*A61M 1/16* (2006.01)
(52) U.S. Cl.
CPC ........ *A61M 1/1662* (2014.02); *A61M 1/1635* (2014.02); *A61M 1/1656* (2013.01); *A61M 1/1658* (2013.01); *A61M 1/1668* (2014.02)

(58) Field of Classification Search
CPC .............. A61M 1/1635; A61M 1/1656; A61M 1/1658; A61M 1/1662; A61M 1/1668
See application file for complete search history.

(56) References Cited

U.S. PATENT DOCUMENTS 3,878,095 A * 4/1975 Frasier ................ A61M 1/1656
210/180
2005/0045540 A1 3/2005 Connell et al.
(Continued)

FOREIGN PATENT DOCUMENTS

| DE | 4211455 | 12/1993 |
|----|---------|---------|
| DE | 19929327 | 12/2000 |

(Continued)

*Primary Examiner* — Dirk R Bass
(74) *Attorney, Agent, or Firm* — Jacobson Holman, PLLC.

(57) ABSTRACT

A dialysis machine has a dialyzer (D), a water inlet system for supplying the dialyzer (D) with fresh dialysis fluid which is connected to the dialyzer and an external water supply and with a line for used dialysis fluid, which is in communication with the dialyzer (D). The water inlet system includes a container for water or other liquid, in particular for RO water. The dialysis machine includes a heat exchanger connected with the line for used dialysis fluid and with the water inlet system so that heat is transferred from the used dialysis fluid to the liquid present in the water inlet system. The container includes means for physical separation of the external water supply and the downstream portions of the water inlet system, preferably a free-fall path for incoming liquid from the water supply, and the heat exchanger is arranged downstream of the container.

18 Claims, 1 Drawing Sheet

(56) References Cited

U.S. PATENT DOCUMENTS

2009/0230043 A1* 9/2009 Heyes ............... A61M 1/1656
                                                   210/182
2014/0014580 A1* 1/2014 Ritter ............... A61M 1/1656
                                                   210/636

FOREIGN PATENT DOCUMENTS

| EP | 2497507 | 9/2012 |
| EP | 2554192 | 2/2013 |
| EP | 2826505 | 1/2015 |
| WO | WO 2008/065470 | 6/2008 |
| WO | WO 2011/112317 | 9/2011 |
| WO | WO 2015/071247 | 5/2015 |

* cited by examiner

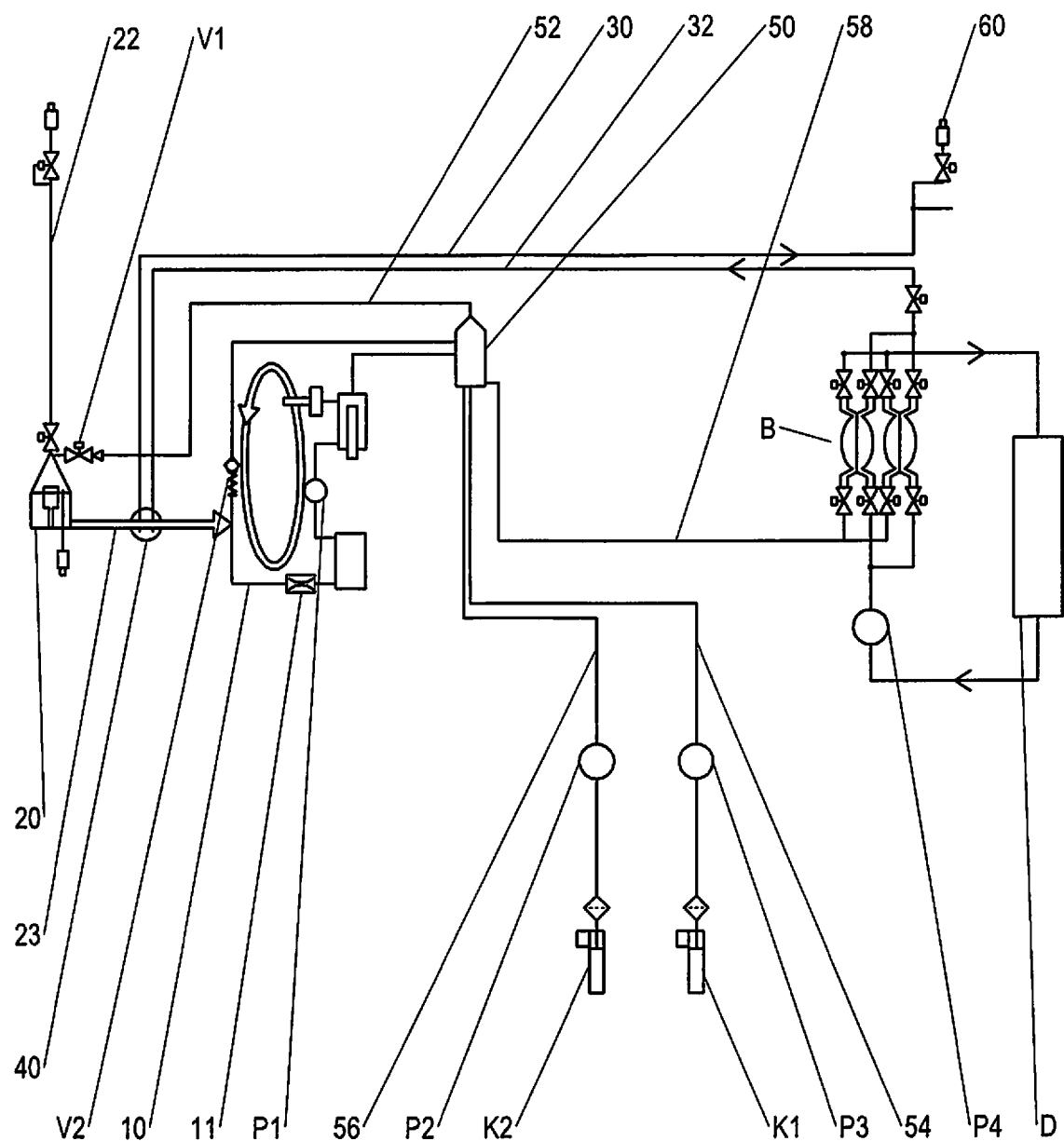

DIALYSIS MACHINE

BACKGROUND OF THE INVENTION

1. Field of the Invention

The present invention relates to a dialysis machine having a dialyzer, a water inlet system connected to the dialyzer and an external water supply for supplying the dialyzer with fresh dialysis fluid and a line connected to the dialyzer for used dialysis fluid, wherein the water inlet system comprises a container, in the following also referred to as water inlet tank, for a liquid, in particular for RO water, and a recirculation circuit, and wherein the dialysis machine has a heat exchanger, which on the one hand is connected to the used dialysis fluid line and on the other hand to the water inlet system, so that heat from the used dialysis fluid is transferred to the liquid in the water inlet system.

2. Description of Related Art

In dialysis machines known in the art, for example, the dialysis fluid is prepared by adding one or more concentrates to fresh RO water, i.e. water which is produced by reverse osmosis. This mixture is fed to the dialyzer when needed.

The RO water used for the production of the dialysis fluid is present in a water inlet tank, which is a part of the recirculation circuit in known devices.

In order to use the heat of the used dialysis fluid, it is further known to use a heat exchanger, which is flowed through on one side by the used dialysis fluid and on the other side by RO water, which is heated in this way.

As the used dialysis fluid could leak into the RO water through a leak in the heat exchanger and thus into the supply system of the dialysis center for the central provision of RO water, countermeasures for polluting the RO water can be used which would prevent such contamination in any case. One of the possible countermeasures is a sensor which detects such a transfer of used dialysis fluid.

The use of a system for preventing the contamination or a sensor and the associated monitoring system is indeed advantageous insofar as a leak of the heat exchanger can be reliably detected, however, associated with the disadvantage of increased cost expenditure.

SUMMARY OF THE INVENTION

The present invention has the object of developing a dialysis machine of the type mentioned above in such a way that it is ensured in a simple manner that RO water of a central supply system is not contaminated.

This object is achieved by a dialysis machine having the features described herein. Accordingly, it is provided that the container comprises means for physically isolating the external water supply and the downstream portions of the water inlet system, preferably a free fall path for incoming liquid from the water supply, and that the heat exchanger is located downstream of the water inlet container. The term "downstream" is to be understood based on the flow direction of the fluid, in particular of the RO water, in the production of the dialysis fluid. Due to the physical separation of the water flow within the water inlet tank and the arrangement of the heat exchanger downstream of the water inlet tank and thus this physical barrier, even if leakage occurs no contamination of the external water supply can occur. Thus, the contamination of the supply line of the clinic or a dialysis center, from which the water inlet tank is fed with RO water, with used dialysis fluid is excluded. Further, a contamination of the supply line, for example, by a disinfectant used in a cleaning of the dialysis machine is thus excluded.

In one embodiment, no sensor is provided for checking whether a transfer of used dialysis fluid to the liquid present in the water input system, which is preferably RO water, has taken place in the heat exchanger. The sensor and the associated evaluation unit can thus be dispensed with.

The term "water inlet tank" includes any tank capable of containing the liquid needed to make the final dialysis fluid, particularly RO water, the tank having means for physical separation of the external water supply and the downstream portions of the water inlet system. It may be a container with fixed walls or a container with flexible walls.

The water inlet tank preferably provides a reservoir for the liquid needed to make the dialysis fluid, e.g. RO water. The water inlet tank preferably has an interface by means of which RO water can be introduced from the external water supply into the water inlet tank. The external water supply can be, for example, a central supply system of a dialysis clinic in which RO water is produced and to which several dialysis machines can be connected. The interface may, for example, be a connection for a water supply line of the supply system.

In one embodiment, as a physical barrier, the water input container comprises a free fall path, wherein liquid coming from the water supply freely falls from a higher initial level to a deeper basin (e.g., flowing or dripping), in which the water is standing, overcoming a height difference. The basin may be connected, for example by means of a siphon tube, to the downstream sections of the water inlet system such that the liquid, after exceeding a certain level of liquid in the basin, flows into the downstream sections of the water inlet system.

In a preferred embodiment of the invention, the water inlet system comprises a recirculation circuit and a line between the water inlet tank and the recirculation circuit. Through this line, the liquid flows, in particular RO water from the container into the recirculation circuit. Said heat exchanger is preferably located in this line and is flowed through on one side by the used dialysis fluid and on the other side by RO water or the like.

In a further preferred embodiment of the invention, it is provided that the water inlet system has a recirculation circuit and that the water inlet tank does not form part of the recirculation circuit. Preferably, the liquid used for the production of the dialysis fluid, preferably the RO water, thus passes from the water inlet tank into the heat exchanger in which it is heated, and then into the recirculation circuit. This increases the effectiveness of the heat exchanger.

Furthermore, it can be provided that the water inlet system has a recirculation circuit and that the dialysis machine has a balancing chamber system which is in communication with the recirculation circuit. In this case, the dialysis fluid produced in the water inlet system passes from the recirculation circuit or from the addition points for concentrates for the preparation of the dialysis fluid (directly or indirectly) into the balancing chamber system of the dialysis machine.

Furthermore, it can be provided that the water inlet system has an air separator. This has the task of separating air so that it does not enter the balancing chamber system and the dialyzer of the dialysis machine. Preferably, the air separator is arranged to separate air from the RO water circulating in the recirculation circuit.

Preferably, the air separator is in the recirculation circuit of the water inlet system.

It is conceivable that a line for air separation between the air separator and the water inlet tank extends, wherein it is preferably provided that there is a valve in the line. By means of the valve, the line can be opened and closed, so that a targeted removal of air from the air separator can take place.

It is possible by the instance of a control or regulating unit to open and close this valve cyclically.

It is possible that the control or regulating unit is designed such that the valve opens and/or closes at a certain time and/or for a certain period of time.

In a further embodiment of the invention, it is provided that the water inlet system has a dosage system, by means of which one or more concentrates can be added. Thus, one or more concentrates, which are required for the production of the finished dialysis fluid, may be added to the initially introduced water, in particular RO water. In this case, a preferred embodiment of the invention is that the water inlet system has a recirculation circuit and the concentrate or concentrates from the one or more concentrate containers can be supplied by one or more lines to the RO water flowing out of the recirculation circuit.

It is conceivable that the dosage system is in communication with the air separator, so that the concentrate or concentrates are introduced into the air separator. It is possible that the dosage system comprises one or more lines, at least one of which opens into a lower region of the air separator.

The air separator may have a first portion and a second portion, wherein the first portion is located below the second portion and wherein the dosage system communicates with the lower portion and said conduit with the upper portion of the air separator.

It is preferred if the lower section of the air separator is connected to the balancing chamber system of the device. From there, the finished dialysis fluid enters the balance chamber system of the device.

The air separator may include a separator plate having one or more openings separating the first from the second portion of the air separator. The separating plate prevents that one or more of the added concentrates enter the upper part of the air separator. The upper part of the air separator is part of the recirculation circuit. The lower part of the air separator is not part of the recirculation circuit and serves as an addition point for the at least one concentrate and for mixing the concentrate with the RO water. This mixture then passes to the dialyzer or to the balancing system which is upstream of the dialyzer. Therefore, the fluid contained in the recirculation circuit, in particular RO water remains free of concentrate.

Another function of the divider plate is that air, which may originate from the concentrate pumps and contained in the concentrate or concentrates (e.g. due to an empty concentrate canister), rises through the bores of the divider plate and thus enters the recirculation circuit in which it is separated.

The water inlet system may comprise a recirculation circuit, wherein means are provided which are designed such that the recirculation circuit is refilled from the water inlet tank when a withdrawal of water from the recirculation circuit to the dialyzer or to the balancing chamber system has taken place. These means may be designed such that the volume is determined, which is taken from the recirculation circuit and a corresponding volume is refilled from the water inlet tank. It is also possible for the means to be designed in such a way that the pressure in the recirculation circuit, which has dropped after the removal of RO water to produce the dialysis fluid, is rebuilt by refilling the recirculation circuit, i.e. is increased. A pressure drop in the recirculation circuit due to a removal of finished dialysis fluid is thus compensated by the fact that fluid is replenished in an amount from the water inlet tank in the recirculation circuit, so that the pressure is rebuilt.

The present invention further relates to a dialysis machine with a dialyzer and with a water inlet system for supplying the dialyzer with fresh dialysis fluid which is connected to the dialyzer and an external water supply, the water inlet system having a recirculation circuit for recirculation of a fluid which is required for the preparation of the dialysis fluid, in particular RO water, wherein in the recirculation circuit, an air separator is arranged, from which a line for air separation leaves and to which a line for supplying a concentrate extends, which extends between a dosage system and the air separator.

The air separator thus has not only the function of air separation, but also serves to receive the one or more concentrates or for mixing of the one or more concentrates with water flowing in the recirculation circuit, in particular with RO water.

The dialysis machine according to this aspect of the invention may be formed according to one or more of the embodiments described herein. So it is conceivable, for example, that the air separator has a partition plate having one or more holes, wherein the line for supplying concentrate is located below the partition plate and the conduit for removing air is located above the partition plate. Preferably, only the area above the partition plate is part of the recirculation circuit.

It should be noted at this point that the use of the term "a or an" is not to be construed as limiting one of the elements concerned. Rather, the terms also include the presence of two or more than two of the elements in question.

BRIEF DESCRIPTION OF THE DRAWINGS

Further details and advantages of the invention will be explained in more detail with reference to an embodiment shown in the drawing.

The sole FIGURE shows a schematic view of a hydraulic system of a dialysis machine according to the invention.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The FIGURE shows a hydraulic system of a dialysis machine according to the invention. The hydraulic system comprises the water inlet tank or container 20 in which RO water is located.

The container 20 is filled with RO water via the watercourse 22, which is assigned, for example, to a central supply system for RO water of a dialysis center.

The reference number 10 indicates a recirculation and degassing circuit in which a solution or a liquid, in particular RO water, which is used to produce the finished dialysis fluid, circulates by means of the pump P1. In addition to further components, a pressure limiting valve V2 and the primary air separator 50 are arranged in the recirculation circuit 10. There is no concentrate in the recirculation circuit. This is added only downstream of the recirculation circuit.

In the recirculation cycle, the RO water is degassed and heated.

As can be seen from the FIGURE, a line 23 extends between the container 20 and the recirculation circuit 10. Via this line 23, the fluid contained in the container 10, in particular RO water, is supplied to the recirculation circuit 10.

As can be seen further from the FIGURE, a conduit 52 runs from the primary air separator 50 to the water inlet tank 20, wherein the conduit 52 is closed by a valve V1 and is opened if necessary. This line 52 serves to remove air from primary air separator 50 via the valve V1 into the container 20. By the separation of air it shall be ensured that fluid or RO water, respectively, present in the recirculation circuit is free of air.

The air is released by the degassing of the RO water, for example, by pump P1 in conjunction with the degassing throttle 11, a negative pressure is generated, which leads to the degassing of the RO water. Another source of air is that one of the concentrate containers K1, K2 is empty. Alternatively or additionally, for example, be provided to degas the water by heating.

The lines 30 and 32 indicate lines for used dialysis fluid, i.e. lines which communicate with the dialyzer and through which the used dialysis fluid flows from the dialyzer. Via the line 32, the used dialysis fluid passes to the heat exchanger 40 and from there via the line 30 to a drain 60.

Reference sign B denotes the balancing system, by means of which it is ensured that the dialysis fluid conveyed to the dialyzer is supplied in the same volume as used dialyzing fluid passing from the dialyzer is discharged. The reference character D denotes the dialyzer, which has a plurality of hollow-fiber membranes, which are flowed around or flowed through by blood on one side and of dialysis fluid and on the other side. As can be seen from the FIGURE, the dialyzer D is connected at its inlet side and at its outlet side with the balancing system B. Reference symbol P4 denotes the dialysis fluid pump which conveys the dialysis fluid. This is arranged downstream of the dialyzer D in the embodiment shown here.

In simplified terms, the reference symbols K1 and K2 denote concentrate containers, for example for a basic and an acidic concentrate. These containers are connected via lines 54, 56 to the lower portion or to the bottom of the primary air separator 50. The concentrates from the concentrate containers K1 and K2 are conveyed by means of the pumps P2 and P3 through the lines 54 and 56. The reference symbols K1 and K2 are preferably flushing chambers for concentrate suction bars.

The circulation in the recirculation circuit 10 is represented by the closed arrow in the middle of the recirculation circuit.

As can be seen from the FIGURE, the heat exchanger 40 is located downstream of the water inlet tank 20 and namely between the water inlet tank 20 and the recirculation circuit.

The water inlet tank 20 has a free fall path, in which RO water running from the central water supply via the water inlet section 22 into the container 20 from a higher initial level falls freely through the air into a lower lying basin. The basin is connected to the pipe 23 by means of a siphon pipe. As a result of this design, the liquid flows into the line 23 after exceeding a certain level of liquid in the basin. Of course, other devices for adjusting the liquid level in the basin or for limiting the flow into the line 23 are also conceivable.

Unlike arrangements known from the prior art in which the heat exchanger is in front of, i.e. upstream, the water inlet container, there is no need according to the invention to check the heat exchanger 40, if there is a leak, because of the used dialysis fluid runs from the line 32 to the water supply path 22 and thus into the central supply device of the dialysis center.

In operation of the illustrated arrangement, the recirculation circuit via the line 23 is fed with RO water and the lower part of the primary air separator 50 is fed with concentrates via the lines 54 and 56. By means of pump P1, these components are mixed to form a finished dialysis fluid.

If the finished dialysis fluid is required for the treatment, it flows from the lower region of the primary air separator 50 via the line 58 into the balancing chamber system B. A correspondingly large volume of RO water flows into the recirculation circuit 10 via the line 23.

As can be seen from the FIGURE, the recirculation of the liquid in the recirculation circuit 10 is not via the water inlet chamber 20, since this is located upstream of the recirculation circuit 10 and forms no part of this. Instead, the recirculation takes place, i.e. downstream of the heat exchanger 40 via a pressure relief valve V2 in a separate water inlet circuit 10.

As stated above, the connection between the primary air separator 50 in the separate water inlet circuit 10 and the water inlet chamber 20 takes place via a valve V1. The resulting air separation can take place cyclically (at a certain time) via the valve, possibly with a certain opening time, into the water inlet chamber 20.

The separate water inlet circuit, which is also referred to above as recirculation circuit 10, supplies the balance chamber B of the device after addition of the one or more concentrates with tempered, mixed dialysis fluid.

As noted, when solution is withdrawn from the recirculation loop 10, i.e. led to the balancing chamber system B, the amount removed from the water inlet chamber 20 is refilled and preheated via the heat exchanger 40 by means of the used dialysis fluid.

As can be seen from the FIGURE, the air separation takes place from the primary air separator 50 in its upper region, which is different from the lower region connected to the recirculation circuit or forms part of it. The supply of concentrates and the removal of the finished dialysis fluid by means of the lines 54, 56 and 58 takes place from the opposite lower portion of the primary air separator.

These two sections of the primary air separator 50 are connected with each other by means of a partition plate with openings for the air separation (in the event of an error with empty canister).

Due to the arrangement of the heat exchanger 40 after the water inlet tank 20 with a free fall distance or other means for physical separation of the downstream hydraulic system of the dialysis machine from the supply line 22 it can be dispensed with comparatively expensive monitoring of leakage of the heat exchanger 40, at the same time the effectiveness the heat exchanger is guaranteed. In the arrangement shown here, the heat exchanger serves to heat the RO water flowing from the water inlet chamber 20 to the circuit 10. For this purpose, the heat exchanger 40 may have a primary side and a secondary side, wherein the primary side is flowed through by the used dialysis fluid and the secondary side through the RO water.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A dialysis machine comprising:
a dialyzer (D);
a water inlet system for supplying the dialyzer (D) with fresh dialysis fluid which is connected to the dialyzer and an external water supply and with a line in communication with the dialyzer (D) for used dialysis fluid, the water inlet system including a container for water or other liquid, a dosage system with which one or more concentrates are addable to a liquid for producing the dialysis fluid, and an air separator, with the dosage system being in communication with the air separator such that the one or more concentrates are introduced into the air separator; and
a heat exchanger in communication with the line for used dialysis fluid and with the water inlet system so that heat is transferred from the used dialysis fluid to the fluid in the water inlet system,
the container including means for physical separation of the external water supply and downstream sections of the water inlet system, and with the heat exchanger being arranged downstream of the container.

2. The dialysis machine according to claim 1, wherein there is no sensor with which it is possible to check whether a transfer of the used dialysis fluid to the liquid present in the water inlet system takes place in the heat exchanger.

3. The dialysis machine according to claim 1, wherein the water inlet system includes a recirculation circuit, and a line between the container and the recirculation circuit, and wherein the heat exchanger is located in the line between the container and the recirculation circuit.

4. The dialysis machine according to claim 1, wherein the water inlet system has a recirculation circuit, and the container forms no part of the recirculation circuit.

5. The dialysis machine according to claim 1, wherein the water inlet system includes a recirculation circuit, and wherein the dialysis machine has a balancing chamber system (B) which communicates with the recirculation circuit, such that the dialysis fluid flows from the recirculation circuit to the balancing chamber system (B).

6. The dialysis machine according to claim 1, wherein a line for air separation is located between the air separator and the container, and wherein a valve (V1) is located in the line for air separation.

7. The dialysis machine according to claim 6, wherein the dialysis machine has a control or regulating unit configured to cyclically open and close the valve (V1).

8. The dialysis machine according to claim 7, wherein the control or regulating unit is configured to at least one of open and close the valve (V1) at at least one of a certain time and for a certain period of time.

9. The dialysis machine according to claim 1, wherein the water inlet system includes a recirculation circuit, and wherein the dosage system is configured such that the one or more concentrates are added downstream of the recirculation circuit.

10. The dialysis machine according to claim 9, wherein the air separator has a first portion and a second portion, wherein the first portion is arranged below the second portion, and wherein the dosage system is in communication with the lower portion, and a line for air separation is in communication with the upper portion of the air separator.

11. The dialysis machine according to claim 10, wherein the lower portion of the air separator is in communication with a balancing chamber system (B) of the dialysis machine and/or the upper portion of the air separator forms a part of the recirculation circuit.

12. The dialysis machine according to claim 10, wherein the air separator has a partition plate with one or more openings therein, which separates the first section from the second section of the air separator.

13. The dialysis machine according to claim 1, wherein the water inlet system includes a recirculation circuit, with the water inlet system being configured such that the recirculation circuit is refilled from the container when a removal of liquid from the recirculation circuit has been carried out.

14. A dialysis machine comprises a dialyzer (D) and a water inlet system for supplying the dialyzer (D) with fresh dialysis fluid which is communicating with the dialyzer (D) and an external water supply, the water inlet system having a recirculation circuit for recirculation of a fluid required for manufacturing the dialysis fluid, in particular of RO water, with, in the recirculation circuit, an air separator being arranged, from which a line for air separation extends and to which a line for supplying a concentrate extends, with the line for supplying the concentrate extending between a dosage system and the air separator.

15. The dialysis machine according to claim 14, further comprising a heat exchanger in communication with a line for used dialysis fluid and with the water inlet system for transferring heat from the used dialysis fluid to the fluid in the water inlet system.

16. The dialysis machine according to claim 1, wherein the water in the container is RO water.

17. The dialysis machine according to claim 1, wherein the means for physical separation of the external water supply and the downstream sections of the water inlet system is a free-fall path for incoming liquid from the water supply.

18. The dialysis machine according to claim 1, wherein the air separator is located in a recirculation circuit of the water inlet system.

* * * * *